(12) United States Patent
Mirzaee

(10) Patent No.: US 6,283,947 B1
(45) Date of Patent: Sep. 4, 2001

(54) LOCAL DRUG DELIVERY INJECTION CATHETER

(75) Inventor: Daryush Mirzaee, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/352,628

(22) Filed: Jul. 13, 1999

(51) Int. Cl.[7] ................................ A61M 25/00
(52) U.S. Cl. ........................ 604/264; 604/103.01
(58) Field of Search .................... 604/96, 192, 194, 604/523, 264, 103.01, 103.02, 104–109, 500, 506, 508, 509

(56) References Cited

U.S. PATENT DOCUMENTS

| | | | |
|---|---|---|---|
| 4,465,072 | 8/1984 | Taheri | 128/348 |
| 4,578,061 | 3/1986 | Lemelson | 604/164 |
| 4,655,746 | 4/1987 | Daniels et al. | 604/53 |
| 4,790,839 | 12/1988 | Ahr | 604/367 |
| 5,049,138 | 9/1991 | Chevalier et al. | 604/265 |
| 5,112,305 | 5/1992 | Barath et al. | 604/96 |
| 5,261,889 | 11/1993 | Laine et al. | 604/164 |
| 5,279,565 | 1/1994 | Klein et al. | 604/105 |
| 5,342,295 | 8/1994 | Imran | 604/43 |
| 5,354,279 * | 10/1994 | Hofling | 604/164 |
| 5,378,230 | 1/1995 | Mahurkar | 604/43 |
| 5,380,307 | 1/1995 | Chee et al. | 604/264 |
| 5,415,637 | 5/1995 | Khosravi | 604/105 |
| 5,419,777 | 5/1995 | Hofling | 604/264 |
| 5,460,618 | 10/1995 | Harreld | 604/264 |
| 5,462,523 | 10/1995 | Samson et al. | 604/30 |
| 5,464,395 | 11/1995 | Faxon et al. | 604/96 |
| 5,523,092 | 6/1996 | Hanson et al. | 424/423 |
| 5,531,679 | 7/1996 | Schulman et al. | 604/65 |
| 5,531,713 | 7/1996 | Mastronardi et al. | 604/263 |
| 5,538,504 | 7/1996 | Linden et al. | 604/53 |
| 5,547,472 | 8/1996 | Onishi et al. | 604/93 |
| 5,554,119 | 9/1996 | Harrison et al. | 604/96 |
| 5,558,642 | 9/1996 | Schweich, Jr. et al. | 604/96 |
| 5,562,630 | 10/1996 | Nichols | 604/164 |
| 5,569,197 | 10/1996 | Helmus et al. | 604/96 |
| 5,626,562 | 5/1997 | Castro | 604/53 |
| 5,643,228 | 7/1997 | Schucart et al. | 604/264 |
| 5,681,281 | 10/1997 | Vigil et al. | 604/96 |
| 5,693,029 | 12/1997 | Leonhardt | 604/264 |
| 5,702,372 | 12/1997 | Nelson | 604/264 |
| 5,709,874 | 1/1998 | Hanson et al. | 424/423 |
| 5,713,863 | 2/1998 | Vigil et al. | 604/104 |
| 5,746,716 * | 5/1998 | Vigil et al. | 604/97 |
| 5,749,845 | 5/1998 | Hildebrand et al. | 604/21 |
| 5,766,152 | 6/1998 | Morley et al. | 604/96 |
| 5,795,318 | 8/1998 | Wang et al. | 604/8 |
| 5,820,586 | 10/1998 | Booth et al. | 604/53 |
| 5,833,658 | 11/1998 | Levy et al. | 604/96 |
| 5,836,940 | 11/1998 | Gregory | 606/15 |
| 5,865,794 | 2/1999 | Castro | 604/53 |
| 5,866,561 | 2/1999 | Ungs | 514/182 |
| 5,868,706 * | 2/1999 | Cox | 604/96 |
| 5,873,852 | 2/1999 | Vigil et al. | 604/52 |
| 5,882,335 | 3/1999 | Leone et al. | 604/96 |
| 5,902,266 | 5/1999 | Leone et al. | 604/53 |
| 5,906,599 | 5/1999 | Kaldany | 604/264 |
| 5,916,195 | 6/1999 | Eshel etal. | 604/96 |
| 5,941,868 | 8/1999 | Kaplan et al. | 604/500 |
| 5,947,890 | 9/1999 | Spencer et al. | 600/3 |
| 5,968,068 | 10/1999 | Dehdashtian et al. | 606/192 |
| 5,971,968 | 10/1999 | Tu et al. | 604/264 |

\* cited by examiner

Primary Examiner—Sharon Kennedy
Assistant Examiner—Ann Y. Lam
(74) Attorney, Agent, or Firm—Skjerven Morrill MacPherson LLP; Theodore P. Lopez

(57) ABSTRACT

A catheter for injecting medication to a specific point within a patient comprises a drug delivery lumen extending from a proximal end of the catheter to an injection port. The catheter comprises a mechanism for angularly pushing the injection port outwardly away from the body of the catheter into an artery wall so that medication can be injected directly into the artery wall.

27 Claims, 10 Drawing Sheets

# LOCAL DRUG DELIVERY INJECTION CATHETER

BACKGROUND OF THE INVENTION

This invention pertains to a catheter for delivering a drug to a specific location within a patient's artery.

It is known in the art to provide catheters for delivering drugs directly into the walls of a patient's artery. An example of such a catheter is described in U.S. Pat. No. 5,746,716, issued to Vigil et al. Vigil's catheter 1 includes a set of injectors 2 for injecting medication into an artery wall 3 (FIG. 1). Injectors 2 are mounted on a balloon 4 which is inflated when it is desired to push injectors 2 into artery wall 3. Unfortunately, injectors 2 extend in a direction perpendicular to the axis of catheter 1. Thus, when catheter 1 is inserted or withdrawn from the patient's vascular system, there is a danger that injectors 2 will drag along and injure artery wall 3.

What is needed is an improved catheter which permits delivery of a drug into the walls of an artery where the drug is believed to be most effective.

What is also needed is a catheter with injectors which will not drag across the artery walls when the catheter is inserted or withdrawn from a patient.

SUMMARY

A catheter in accordance with an embodiment of the invention comprises an injection port at or near the distal end thereof and a mechanism for directing the injection port angularly away from the central axis of the catheter and into the artery wall. (An injection port is a structure used for introducing medication or other material into a patient. The injection port typically is a hollow needle.) In one embodiment, the catheter includes a guide wire lumen for receiving a guide wire that enables a physician to direct the catheter to a desired location within the patient's vascular system. Also, in one embodiment, the catheter includes a plurality of needles, each of which may be manipulated at an angle outwardly from the central longitudinal axis of the catheter so that the needles can inject a drug or medication into the surrounding tissue. Prior to deployment of the needles, the needles are retained such that they lie substantially parallel to the longitudinal axis of the catheter.

In one embodiment, a balloon is provided towards the distal end of the catheter for pushing the needles outwardly into the artery wall. In another embodiment, other mechanical means are provided for pushing the needles outwardly.

These and other features of the invention are described below.

BRIEF DESCRIPTION OF THE DRAWINGS

FIG. 3' illustrates an enlarged portion of the catheter of FIG. 3.

DETAILED DESCRIPTION

Figure 1:
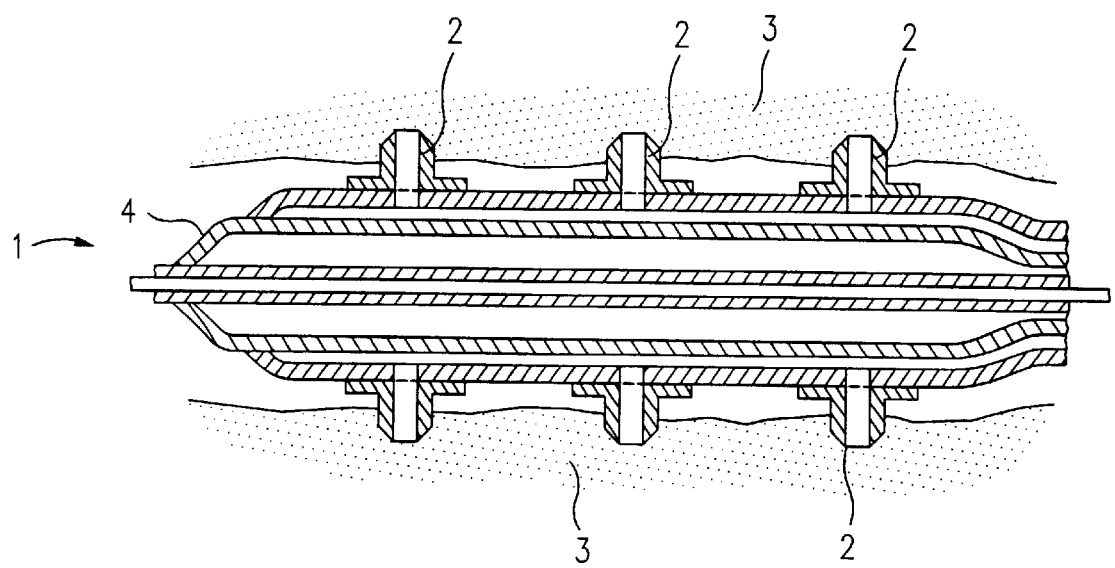
FIG. 1 illustrates a prior art catheter for injecting medication into a patient's artery walls.
Figure 2:
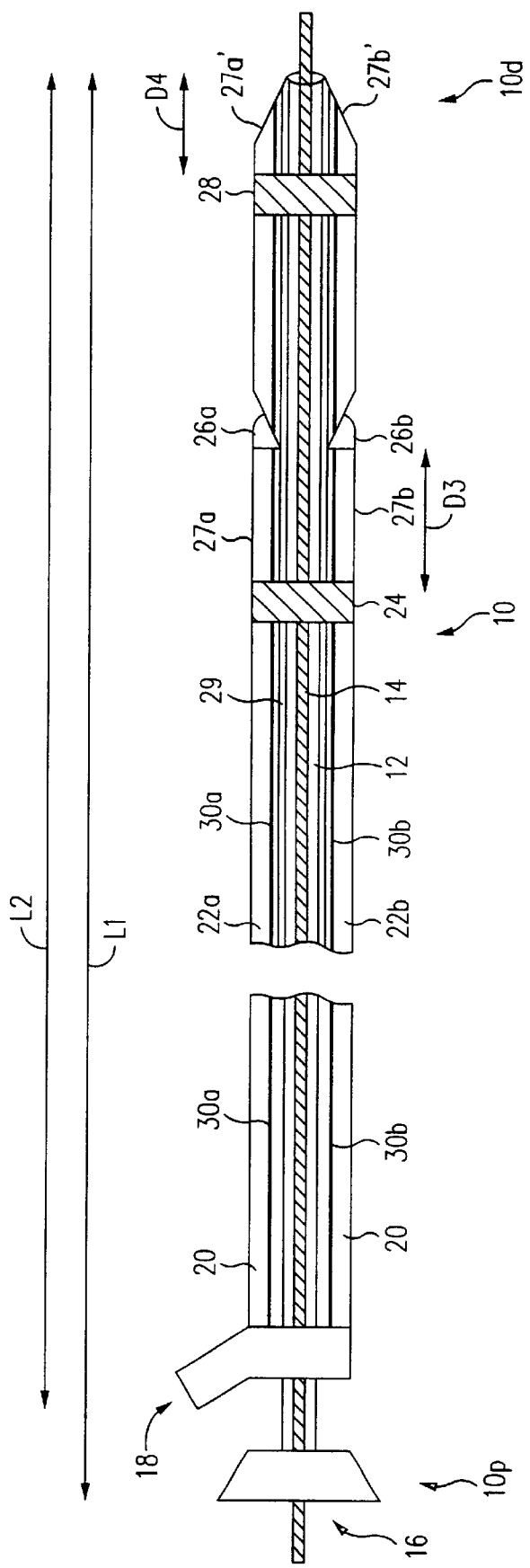
FIG. 2 illustrates in cross section a catheter constructed in accordance with the invention comprising needles for injecting medication into an artery wall.
Figure 3:
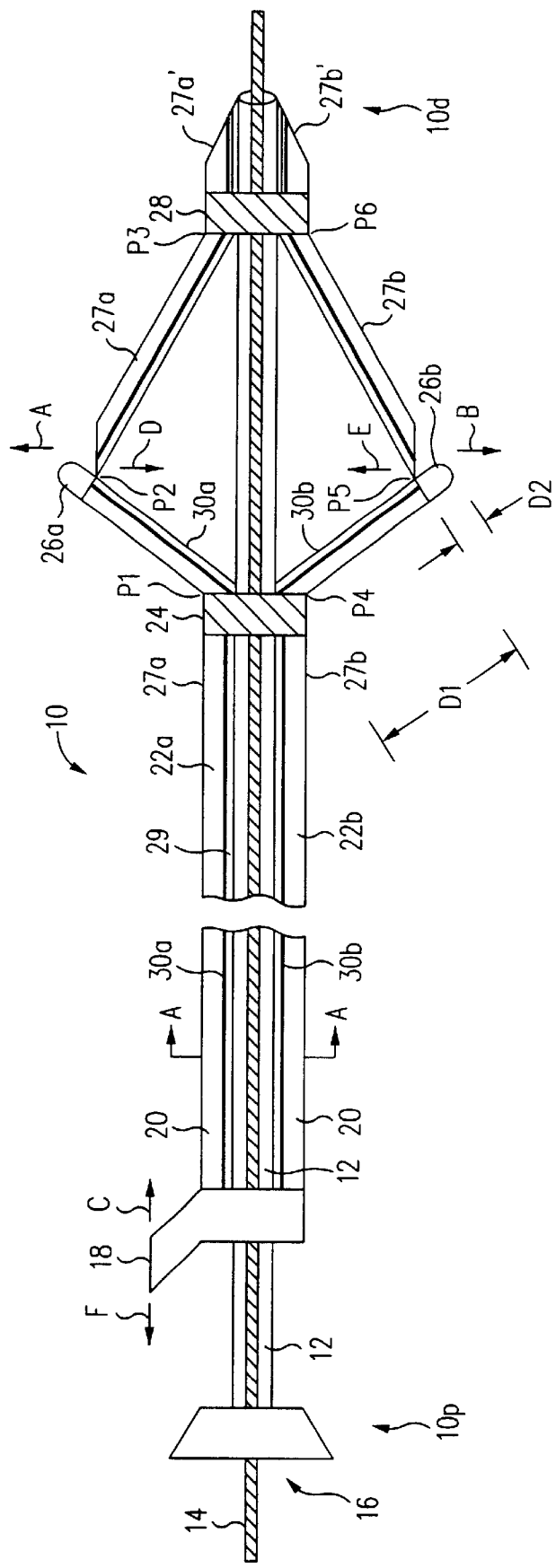
FIG. 3 illustrates in cross section the catheter of FIG. 2 in which the needles are extended outwardly for injecting medication into the artery wall.
Figure 3:
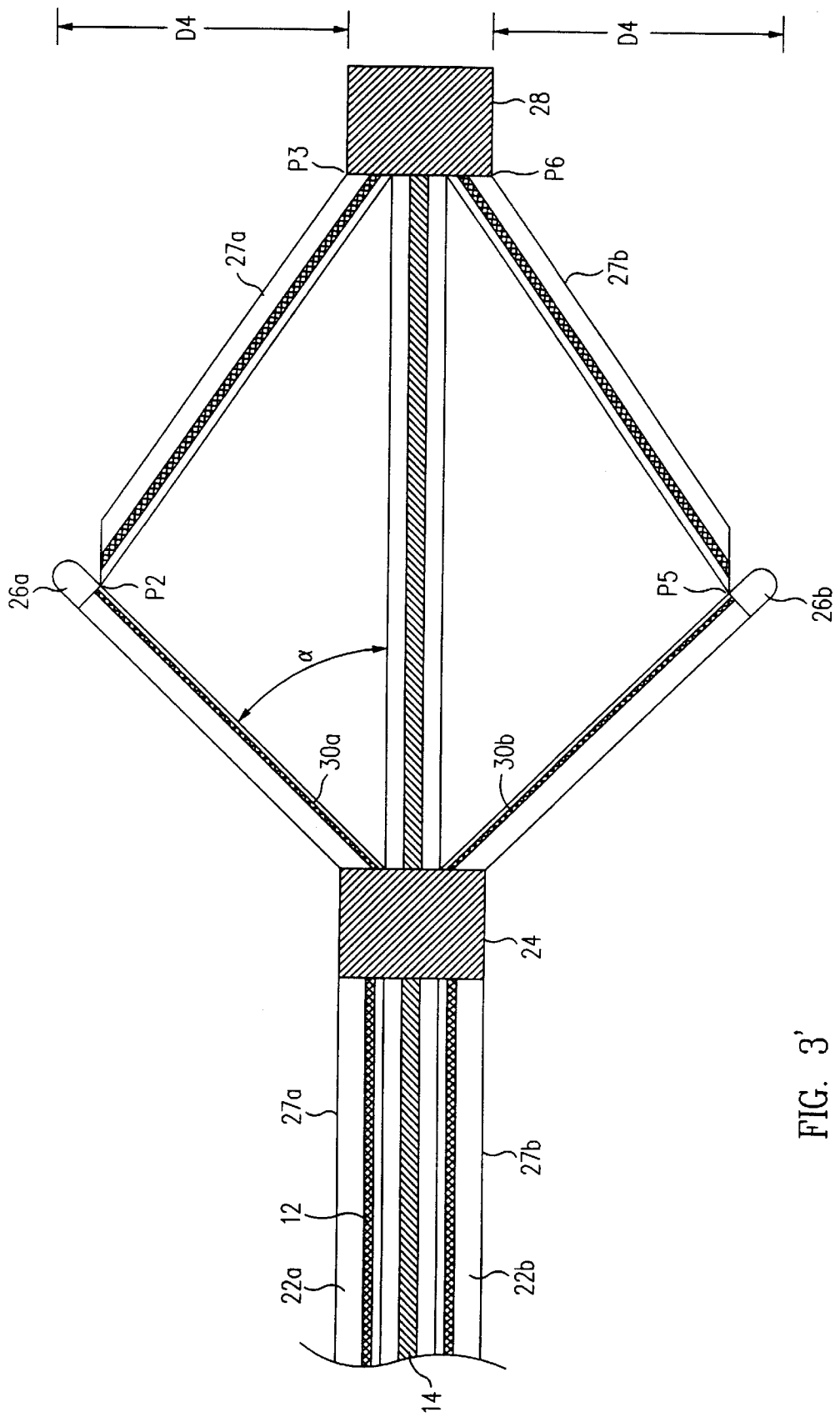

Referring to FIGS. 2, 3 and 3', a catheter 10 in accordance with an embodiment of the invention includes a proximal end 10p, a distal end 10d and a centrally located guide wire tube 29 having a lumen 12 for receiving a guide wire 14. Thus, prior to use, an attending physician can route guide wire 14 into the patient and insert catheter 10 over the guide wire to a desired location within the patient's vascular system. Once catheter 10 is in place, guide wire 14 extends through lumen 12 and out of a guide wire control port 16.

Also within catheter 10 is a drug delivery port 18 for receiving a drug to be injected into the patient. Drug delivery port 18 is connected to a drug delivery lumens 22a, 22b. (In one embodiment, not shown, lumens 22a and 22b can merge into a single lumen concentrically surrounding guide wire tube 29.)

Although FIGS. 2, 3, and 3' illustrate two lumens 22a, 22b, other numbers of lumens for delivering drugs can also be used, e.g., between two and four lumens. However, the invention is not limited by the exact number of drug delivery lumens 22.

Figure 3B:
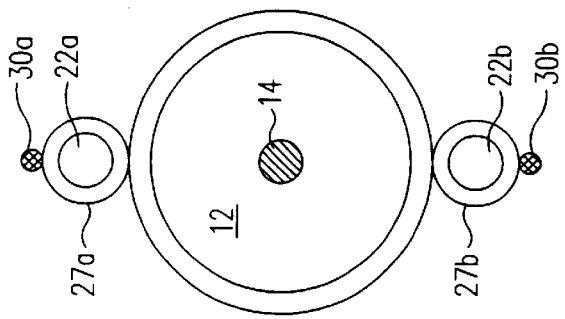
FIG. 3B illustrates in cross section an alternative embodiment of a catheter along lines A—A in which a stiffening mandrel is provided external to two of the catheter tubes.
Figure 3D:
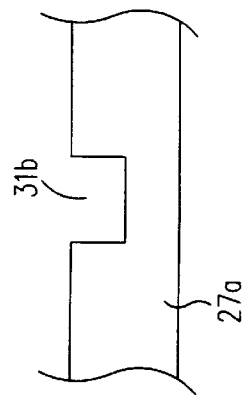
FIG. 3D illustrates another cut formed in a tube to accommodate placement of a needle.
Figure 3A:
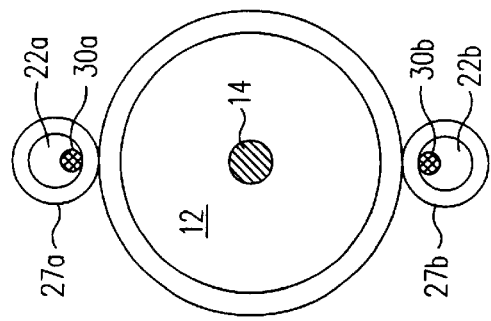
FIG. 3A illustrates in cross section the catheter of FIGS. 2 and 3 along lines A—A.
Figure 3C:
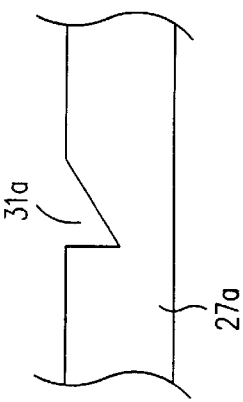
FIG. 3C illustrates a cut formed in a tube to accommodate placement of a needle.

A shrink tube 24 approximately 1 to 6 cm from distal end 10d of catheter 10 binds tubes 27a, 27b (surrounding lumens 22a, 22b) together. Shrink tube 24 is affixed to tube 27a, 27b, but surrounds and can slide along guide wire tube 29. At a distance D1 from shrink tube 24, tubes 27a, 27b are sliced around a circumferential portion of approximately 180°, and hollow needles 26a, 26b, are inserted into lumens 22a, 22b respectively. (The slice formed in tubes 27a and 27b can have different shapes. FIGS. 3C and 3D illustrate two embodiments of slices 31a, 31b that can be formed in tubes 27a and 27b to accommodate needle placement. The slices 31a, 31b help create a preferential bending position for tubes 27a and 27b and are sized to facilitate needle placement.) Needles 26a, 26b can be held in place within lumens 22a, 22b, for example, by an appropriate adhesive (e.g. cynoacrylate). Tubes 27a, 27b continue distally of needles 26a, 26b. Tubes 27a, 27b terminate at distal end 10d of catheter 10, and are bound together and to guide wire tube 29 with second shrink tube 28. (Shrink tube 28 cannot move relative to tube 29.) Needles 26a, 26b are typically located half way between shrink tube 28 and shrink tube 24. The very ends 27a', 27b' of tubes 27a, 27b may be open or sealed.

In one embodiment, shrink tubes 24 and 28 are located at preferential bending positions of tubes 27a and 27b. Because tubes 27a, 27b are not bound to tube 29 along the entire length of catheter 10, this permits relative motion of portions of tubes 27a, 27b and tube 29. (As explained below, during use, moving tubes 27a and 27b relative to tube 29 pushes needles 26 outwardly into the artery wall or inwardly towards guide wire tube 29.) The fact that tubes 27a, 27b are not rigidly bound to tube 29 by shrink tube 24 facilitates bending of the tubes 27a, 27b.

Referring to FIG. 3, in accordance with the first embodiment of the invention, after catheter 10 is in its proper position within the patient's vascular system, a physician extends needles 26a, 26b outwardly (in directions A and B, respectively) by sliding drug delivery port 18 in a forward direction (see arrow C) relative to guide wire control port 16.

A portion of catheter 10 is shown in greater detail in FIG. 3'. The movement of drug delivery port 18 relative to guide wire control port 16 causes a first body portion of catheter 10 comprising tubes 27a and 27b to move relative to a second body portion comprising tube 29. Portions P1, P2 and P3 of tube 27a and portions P4, P5 and P6 of tube 27b act as hinges, permitting needles 26a, 26b to move outwardly. In this way, needles 26a, 26b are pushed away at an angle α from the main axis of catheter 10 and into the artery wall of the patient.

In other words, during insertion and placement of catheter 10, needles 26a, 26b and the portions of tubes 27a, 27b connected to needles 26a, 26b lie substantially parallel to guide wire 14 (i.e., α=0°). When the needles 26a, 26b are deployed, portions P1, P2 serve as axes of rotation for the needles 26a, 26b and the portions of tubes 27a, 27b connected to needles 26a, 26b. Needles 26a, 26b are rotationally pushed away such that portions of tubes 27a, 27b connected to needles 26a, 26b thus form an angle α>0°. When deployed, needles 26a, 26b extend outwards from the main body of catheter 10 by a distance D4, thereby contacting the artery wall.

The attending physician can then inject medication through drug delivery lumens 22a, 22b and needles 26a, 26b into the wall of the patient's artery. Such medication can be, for example, an anti-inflammatory, anti-restenotic, or anti-thrombotic medication. Thereafter, the physician can retract needles 26 in directions D and E by pulling drug delivery port 18 in a direction F relative to guide wire control port 16. Catheter 10 can then be retracted from the patient.

In one embodiment, needles 26a, 26b are stainless steel, have an inner diameter of 0.002" to 0.010" and an outer diameter of 0.005" to 0.014", extend a distance D2 (FIG. 3) of 1 to 3 mm outside of tubes 27a, 27b, and have a total length of 3 to 8 mm. However, other needle sizes can also be used. Catheter 10 can be designed such that distance D4 is customized to facilitate better deployment into different size arteries, e.g. coronary or peripheral. Needles 26a, 26b can be blunt, as shown in FIG. 3, or sharp.

The distance D3 (FIG. 2) between shrink tube 24 and the point where needles 26a, 26b exit from tubes 27a, 27b is between 2 to 10 mm. Distances D2 (FIG. 3) and D3 (FIG. 2) are chosen based on the caliber of the artery in which catheter 10 is to be used. The greater the artery caliber, the greater the total distance D2 plus D3. This is done to ensure that needles 26 reach the artery wall when they are outwardly extended.

In one embodiment, a catheter in accordance with the invention can be the length L1 (FIG. 2) of conventional balloon dilatation catheters, e.g., 40 to 200 cm. The sliding portion of catheter 10 can have a distance L2 (FIG. 2) between 35 and 195 cm. Shrink tube 28 can be a distance D4 (FIG. 2) between 2 and 30 mm from the distal end of catheter 10. However, other lengths and distances can also be used.

Stiffening mandrels 30a, 30b can be provided within lumens 22a, 22b of tubes 27a, 27b as shown in FIGS. 2, 3, 3', 3A and 3B. In one embodiment, the distal ends of mandrels 30a, 30b (e.g. the distal 1 to 20 mm) can be flatter than the proximal ends of mandrels 30a, 30b. Optionally, notches can be formed in stiffening mandrels 30a and 30b to facilitate preferential bending at the location of the notches. In another embodiment, the mandrels are a shape memory alloy such as nitinol having a preferential bend formed therein. In lieu of placing mandrels 30a, 30b within lumens 22a, 22b, stiffening mandrels 30a, 30b can be affixed to the exterior of tubes 27a, 27b as shown in FIG. 3B.

The mandrels are typically 0.003" to 008" wide. If the mandrels are not within lumens 22a and 22b those lumens are typically 0.006" to 0.016" wide (i.e. an inner diameter of 0.006" to 0.016"). If the mandrels are within lumens 22a and 22b, lumens 22a and 22b are typically 0.009" to 0.020" wide.

Guide wire lumen 12 is typically about 0.010" to 0.040" wide depending upon where the catheter is to be used. For coronary artery applications, lumen 12 is about 0.012" to 0.018" wide. For peripheral arteries, lumen 12 can be as wide as 0.040".

Figure 4:
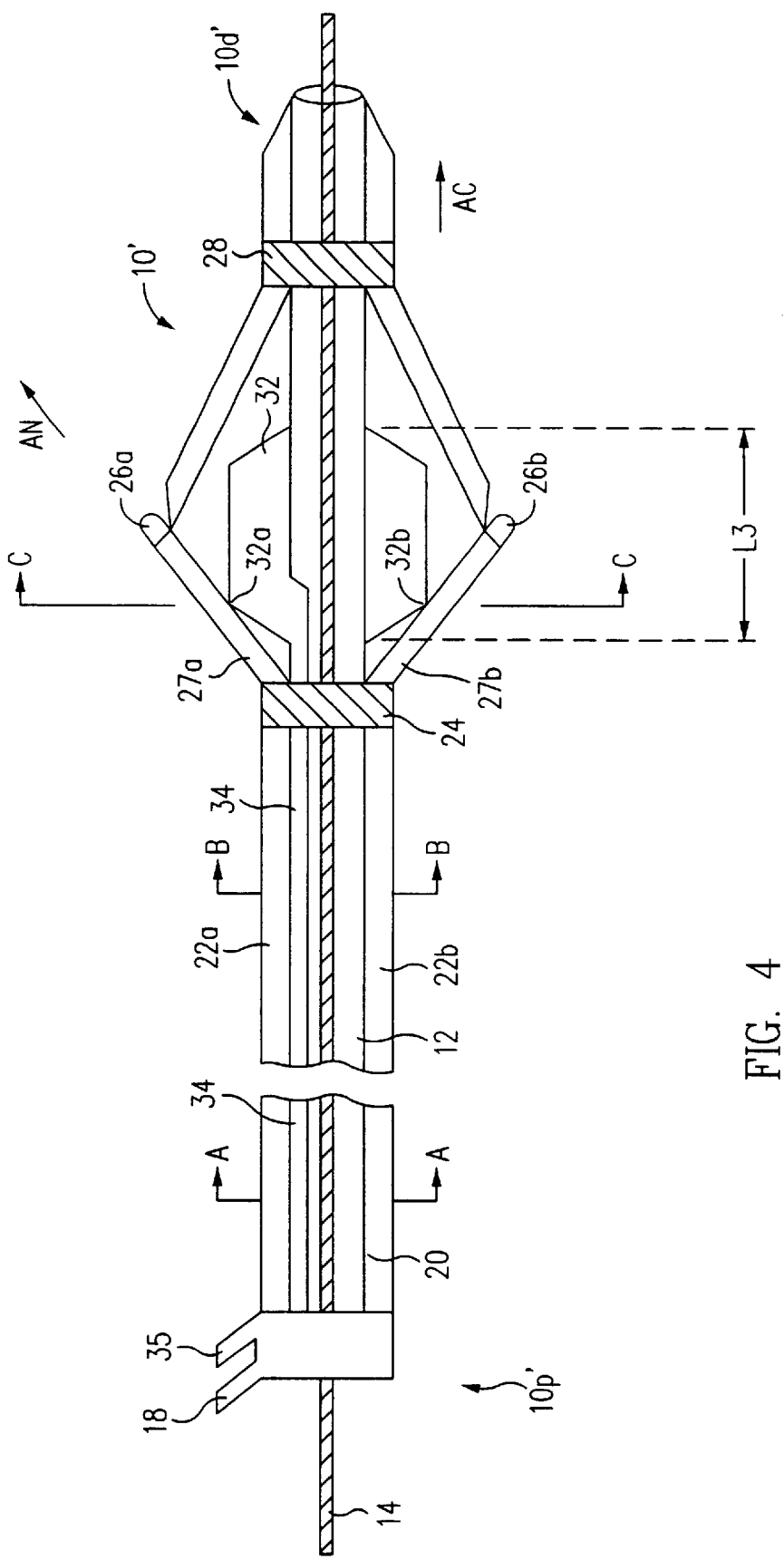
FIG. 4 illustrates another embodiment of a catheter including a balloon for pushing needles from the catheter outwardly into the artery wall.

FIG. 4 illustrates an alternative embodiment of the invention in which a catheter 10' includes a balloon 32 coupled to a balloon inflation lumen 34. Balloon 32 can be constructed in the same manner as a PTCA (percutaneous transluminal coronary angioplasty) balloon. Alternatively, balloon 32 can be doughnut shaped.

Operation of catheter 10' is similar to that of catheter 10 shown in FIGS. 2 and 3. A physician first inserts guide wire 14 into the patient, and then advances catheter 10' over guide wire 14 until hollow needles 26a, 26b are at an appropriate location. When it is desired to insert needles 26a, 26b into the patient's artery wall, a physician injects inflation fluid through a balloon inflation port 35 at the proximal end 10p' of catheter 10' through balloon inflation lumen 34 into balloon 32. Balloon 32 then expands and pushes needles 26a, 26b outwardly into the artery wall. In other words, needles 26a, 26b are rotated outwardly away from the longitudinal axis of catheter 10' (Arrow AC in FIG. 4 is parallel to the longitudinal catheter axis. Arrow AN is the longitudinal needle axis.) During this process, the points adjacent where tube 27a, 27b contact shrink tube 24 act as a hinge. Drugs can then be injected through drug delivery port 18, single drug delivery lumen 20, lumens 22a, 22b and needles 26a, 26b. Thereafter, needles 26a, 26b are retracted by deflating balloon 32 (i.e., by withdrawing inflation fluid from balloon 32 via balloon inflation lumen 34 and balloon inflation port 35). Catheter 10' is then withdrawn from the patient. Balloon 32 is typically affixed to tubes 27a, 27b at points 32a, 32b with an adhesive such as epoxy. (Alternatively, balloon 32 can be affixed to tubes 27a, 27b by other methods, such as welding.) Thus, when balloon 32 is deflated and contracts, it rotationally pulls needles 26 inwardly and substantially parallel to the longitudinal catheter axis AC so that needles 26 will not drag along the artery wall when the catheter 10' is retracted. (In other words, the longitudinal needle axes AN are rotated to be substantially parallel to the longitudinal catheter axis AC.) Although not shown in FIG. 4, tubes 27a, 27b can include mandrels 30a, 30b to enhance their stiffness, as described above with respect to FIGS. 2, 3, 3A, and 3B.

Balloon 32 can be shaped like a conventional dilatation catheter balloon (e.g. the same length and profile). Alternatively, balloon 32 may be shorter than a conventional dilatation catheter. In one embodiment, balloon 32 has a length L3 between 3 and 10 mm.

As can be seen, in the embodiment of FIG. 4, the proximal portion 10p' of catheter 10' includes a single drug delivery lumen 20 which divides into two (or more) lumens 22a, 22b. In the embodiment shown in FIG. 4E, the distal end 10d' of catheter 10' which includes shrink tube 28 (as shown in FIG. 4), is not included.

Figure 4B:
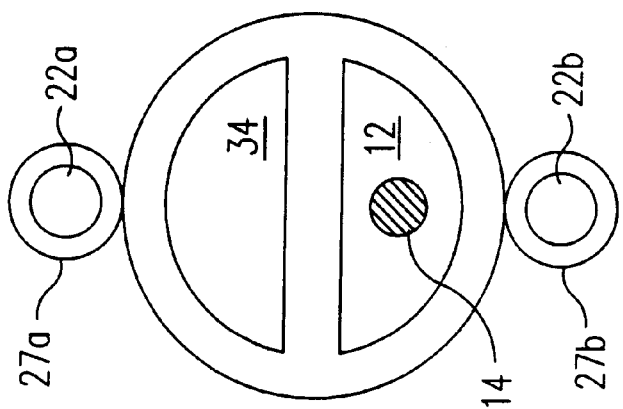
FIGS. 4A, 4B and 4C illustrate in cross section the catheter of FIG. 4 along lines A—A, B—B and C—C, respectively.
Figure 4A:
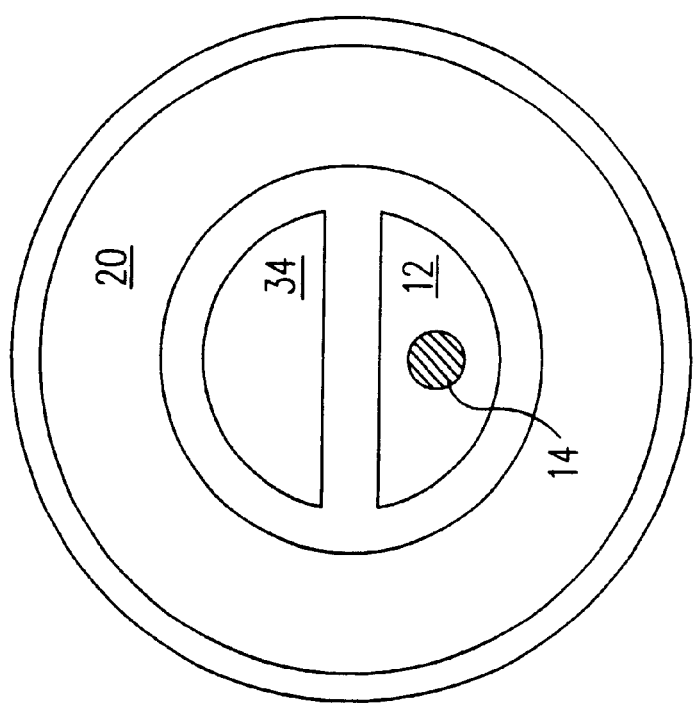
Figure 4D:
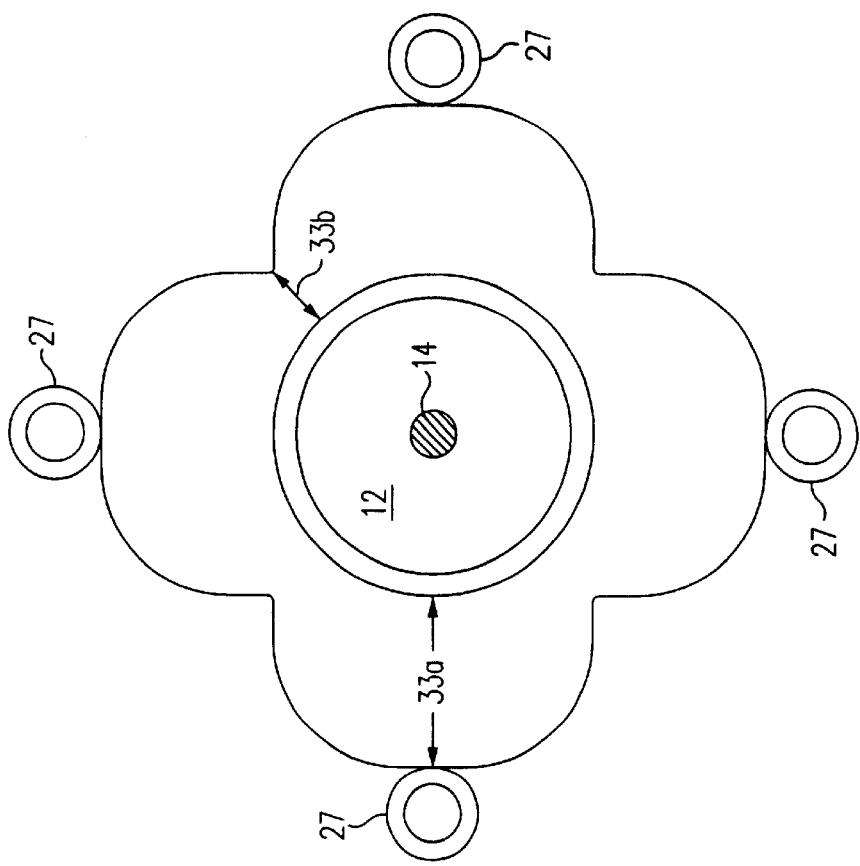
FIG. 4D illustrates in cross section an alternative balloon used in conjunction with another embodiment of a catheter in accordance with the invention.
Figure 4C:
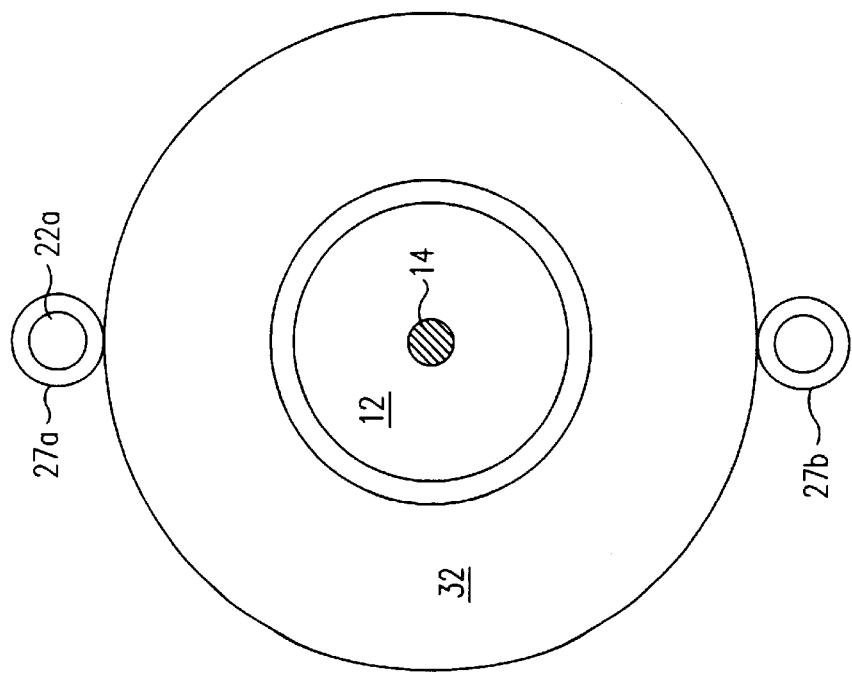

FIGS. 4A, 4B, and 4C illustrate in cross section portions of catheter 10' along lines A—A, B—B, and C—C, respectively. FIG. 4A shows single drug delivery lumen 20, balloon inflation lumen 34, guide wire lumen 12, and guide wire 14. FIG. 4B shows a cross sectional portion of catheter 10' after single drug delivery lumen 20 has divided into two drug delivery lumens 22a, 22b surrounded by tubes 27a, 27b. Finally, FIG. 4C illustrates a cross-sectional view of catheter 10' along line C—C, with inflated balloon 32 pushing tubes 27a, 27b in an angle away from the longitudinal axis of catheter 10'. While FIGS. 4, 4A, 4B, and 4C illustrate a single drug delivery lumens 20, in other embodiments a single drug delivery lumens 20 is not used, and lumens 22a, 22b extend to drug delivery port 18.

As with the embodiment of FIG. 3, the length of the portion of tubes 27a, 27b distal to shrink tube 24 can vary. In one embodiment, when needles 26a, 26b are in their extended position, they only extend a short distance past the top of balloon 32. In other embodiments, needles 26a, 26b can extend a longer distance past the top of balloon 32.

Figure 5:
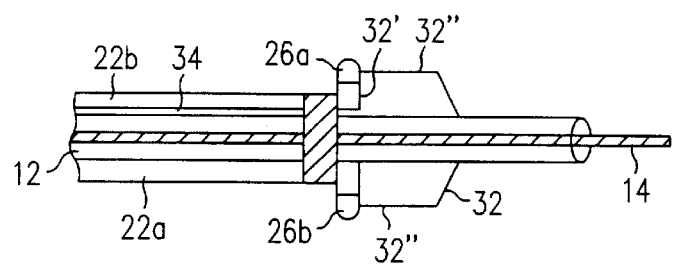
FIG. 5 illustrates in cross section a modified embodiment of the catheter of FIG. 4 including a short balloon length with a steep proximal balloon wall.

FIG. 5 illustrates a catheter similar to that of FIG. 4 except that a balloon 32 has a short length. When balloon 32 is inflated, proximal end 32' of balloon 32 forms a steep step. Needles 26a, 26b extend only a very short distance beyond surface 32" of balloon 32, and are deployed at a near-perpendicular angle with respect to the longitudinal catheter axis in FIG. 5. However, when balloon 32 is deflated, needles 26a, 26b are brought to an angle parallel or substantially parallel to the longitudinal catheter axis.

Figure 4E:
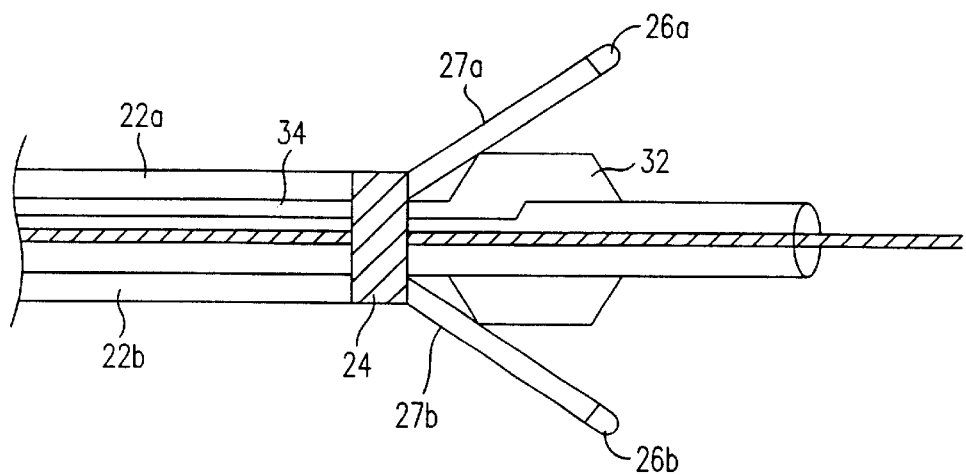
FIG. 4E illustrates another embodiment of a catheter including a balloon for pushing needles from the catheter outwardly into the artery wall.

In FIGS. 4, 4E, and 5, balloon 32 is substantially cylindrical. However, FIG. 4D illustrates in cross section along lines C—C an embodiment of a catheter comprising a balloon 33 which, when inflated, has a clover-like cross section including large wide sections 33a and narrow sections 33b. Narrow sections 33b advantageously permit blood to perfuse past balloon 33 when the catheter is being used and balloon 33 is inflated.

FIG. 4D shows four tubes 27 instead of two tubes 27a, 27b. However, as mentioned above, different numbers of tubes 27 can be used.

Figure 6:
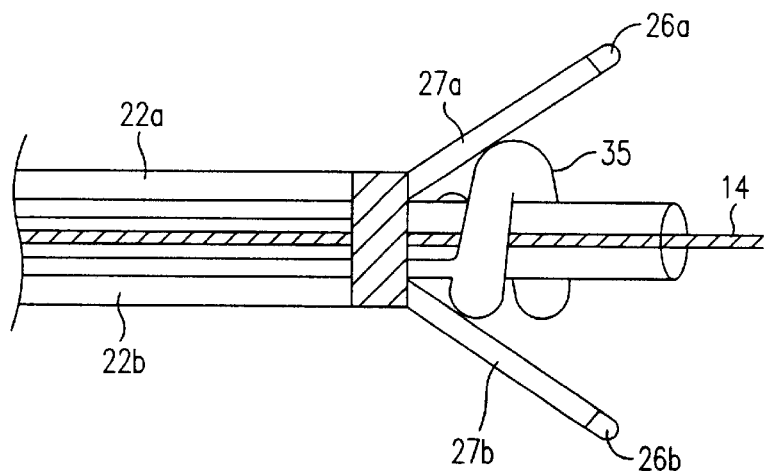
FIG. 6 illustrates the distal end of a catheter including a helical balloon in accordance with another embodiment of the invention.

In lieu of the balloon shapes shown in FIGS. 4, 5, and 4D, a helical balloon 35 as shown in FIG. 6 can be employed. The helical shape of balloon 35 facilitates blood perfusion past balloon 35 during use.

Figure 7:
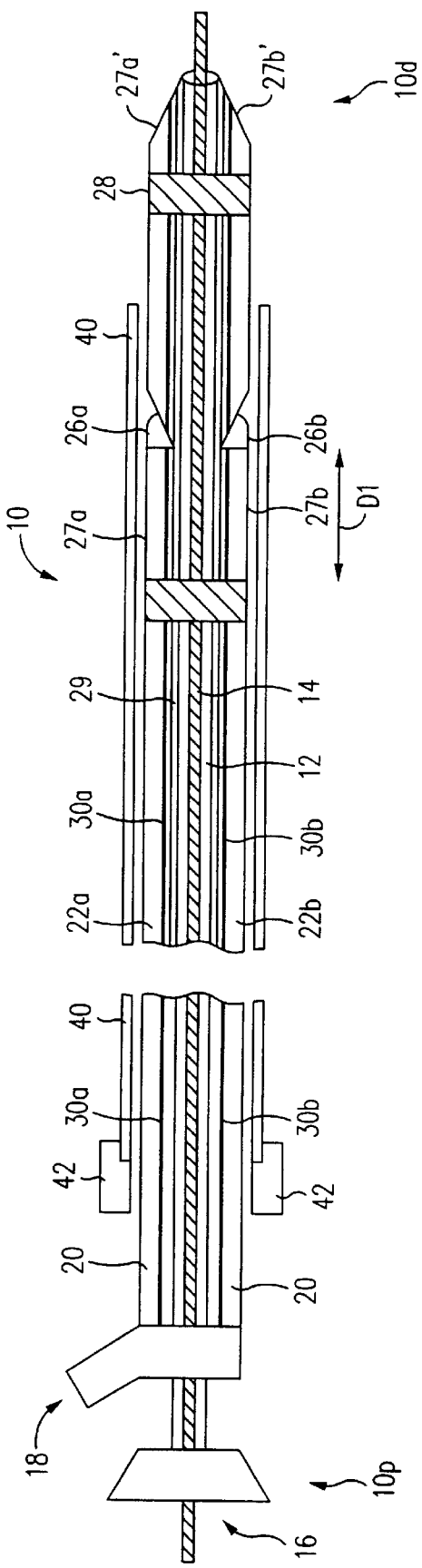
FIG. 7 illustrates a catheter in accordance with the invention in conjunction with a sheath.

In the above embodiments, the catheter in accordance with the present invention may be used in conjunction with a thin cylindrical sheath 40. FIG. 7 shows catheter 10 of FIG. 2 used in conjunction with a sheath 40 that may be used to surround a portion of catheter 10 to cover needles 26a, 26b (and balloon 32, 33, or 36, in the case of an embodiment including a balloon 32, 33, or 36). Sheath 40 keeps needles 26a, 26b close to the catheter body, thereby ensuring a low profile, and ensuring that needles 26a, 26b stay aligned with the longitudinal axis of catheter 10. When catheter 10 is inserted into the patient's blood vessel at the desired position, sheath 40 extends proximally out of the patient's blood vessel so that the physician can manipulate the sheath 40. A sheath removal handle 42 is affixed to the proximal end of sheath 40. Sheath 40 may be pulled back once the catheter 10 is at a desired position before extending needles 26a, 26b and delivering the drug or medication. After use, sheath 40 can be advanced in the distal direction to again cover needles 26a, 26b prior to retracting the catheter 10.

In the above-described embodiments, various structures in the catheter 10 can be formed from radiopaque materials so that the position of catheter 10 may be easily observed during use. For example, the needles 26a, 26b may be radiopaque. This can be accomplished, e.g., by plating needles 26a, 26b with or constructing needles 26a, 26b from a radiopaque material such as titanium or tungsten. Alternatively, radiopaque materials may be placed on the catheter near needles 26a, 26b or preferential bending points P1 to P6. Alternatively, radiopaque materials may be placed on the balloon 32, 33, 36.

The above-described embodiment incorporates shrink tubing, e.g., shrink tubes 24 and 28, to hold various tubes of the catheter 10 together. In lieu of, or in addition to such shrink tubing, the various catheter tubes can be held together by other means, e.g., adhesive heat fusing. Alternatively, the tubes can be coextruded together and then separated by cutting at those locations where the tubes must be permitted to slide relative to one another.

A catheter 10 in accordance with the invention has numerous advantages:

1) The catheter 10 permits blood perfusion (i.e. blood flow around the catheter 10), enabling the catheter 10 to remain within the blood vessel for as long as deemed necessary by the attending physician. This is because the catheter 10 does not block the entire artery lumen even when needles 26a, 26b are extended outwardly.
2) The catheter 10 is typically very flexible, permitting access to distal, tortuous arteries. The reason for this is that the stiff portion of the catheter 10 (the portion of the length along which needles 26a, 26b extend) is very small.
3) While the catheter is being positioned, needles 26a, 26b lie in the axial direction of catheter 10 substantially parallel to the longitudinal axis AC of catheter 10, thereby minimizing the profile of the catheter 10 and minimizing the chance of injury to the artery.

While the invention has been described with regard to specific embodiments, those skilled in the art will recognize that changes can be made in form and detail without departing from the spirit and scope of the invention. For example, the material from which the catheter is made can be any extruded polymer or metal, including shape memory metals or a combination thereof. Also, although the embodiments of FIGS. 2 to 7 contain a guide wire lumen 12, and are used in conjunction with a guide wire 14, other embodiments are not used in conjunction with a guide wire 14. In alternative embodiments, a guide wire 14 is not used, and the space which would otherwise be occupied by guide wire lumen 12 is sealed.

In yet another embodiment, guide wire lumen 12 does not extend the entire length of catheter 10. Instead, guide wire lumen 12 terminates between 1 and 35 cm from distal end 10d of catheter 10, and guide wire 14 extends through only the distal 1 to 35 cm of catheter 10. This facilitates rapid exchange of catheter 10 over guide wire 14.

In yet another embodiment, the catheter can contain other lumens for performing other functions. For example, one can place balloons proximal to shrink tube 24 and distal to shrink tube 28 to prevent medication from diffusing away from the injection site.

Needles 26a, 26b can extend greater or lesser distances D2 past tubes 27a, 27b. Also, in some embodiments, tubes 27a, 27b and needles 26a, 26b can be extended at angles closer to or further from right angles than illustrated in FIGS. 3 to 6. The angle at which tubes 27a, 27b and needles 26a, 26b are extended is typically between 45 and 100°.

In some embodiments, the catheter is used in vessels other than arteries. Accordingly, all such changes come within the invention.

I claim:

1. A catheter for delivering a drug to a location within a patient, comprising:
   a first tube;
   a second tube extending from a proximal end to a distal end along an axis;
   a first lumen provided in said first tube for receiving said drug, said first lumen extending from the proximal end of said first tube to an injection port;
   a preferential bending point on said first tube;
   a balloon lumen provided in said second tube; and
   a balloon coupled to the balloon lumen such that inflation of the balloon bends the first tube at the preferential bending point, thereby angularly pushing said injection port away from the axis of the second tube to change an angle formed between said injection port and said axis of the second tube.

2. Catheter of claim 1 wherein said injection port comprises a needle.

3. Catheter of claim 1 wherein said injection port is radiopaque.

4. Catheter of claim 1 wherein a radiopaque marker is provided on said balloon.

5. Catheter of claim 1 wherein a radiopaque marker is formed on said catheter proximate to said balloon.

6. Catheter of claim 1 wherein a radiopaque marker is provided on said first tube at said preferential bending point where said injection port bends away from said axis of said second tube.

7. Catheter of claim 1 further comprising a stiffening mandrel extending through said first lumen.

8. Catheter of claim 1 further comprising a stiffening mandrel extending along the exterior of said first tube.

9. Catheter of claim 1 wherein said balloon is a helical-shaped balloon.

10. Catheter of claim 1 wherein said balloon has wide and narrow regions to permit blood to perfuse past said balloon when said balloon is inflated.

11. Catheter of claim 1, further comprising a guide wire lumen having an axis parallel to the axis of the second tube.

12. A catheter for delivering a drug to a location within a patient comprising:
   a first tube;
   a second tube extending from a proximal end to a distal end along an axis;
   a first lumen provided in said first tube for receiving said drug, said first lumen extending from the proximal end of said first tube to an injection port;
   a preferential bending point on said first tube;
   a balloon lumen provided in said second tube; and
   a balloon coupled to the balloon lumen such that inflation of the balloon bends the first tube at the preferential bending point, thereby rotating said injection port away from the axis of the second tube.

13. Catheter of claim 12, further comprising a guide wire lumen having an axis parallel to the axis of the second tube.

14. Method for delivering medication to a patient comprising the steps of:
   inserting a catheter into a patient, said catheter comprising a catheter body, a drug delivery lumen within the catheter body, and an injection port in communication with said drug delivery lumen;
   inflating a balloon to angularly push the injection port away from the catheter axis toward or into the patient's artery wall by bending said drug delivery lumen at a preferential bending point; and
   injecting medication into the patient through the drug delivery lumen and said injection port.

15. Method of claim 14 wherein said injection port is a needle.

16. Method of claim 14 further comprising the steps of:
   moving said injection port toward an angle parallel with the axis of said catheter after said step of injecting; and
   retracting said catheter.

17. A catheter for delivering a drug to a location within a patient, comprising:
   a guide wire lumen;
   a tube extending from a proximal end to a distal end along an axis of said guide wire lumen and having a first lumen for receiving said drug, said first lumen extending from the proximal end of said tube to an injection port;
   a preferential bending point on said tube; and
   a balloon for angularly pushing said injection port away from the axis of the guide wire lumen by bending said tube at said preferential bending point, thereby changing an angle formed between said injection port and said axis of the guide wire lumen;
   said injection port being coupled to said tube at said preferential bending point.

18. Catheter of claim 17 wherein said injection port comprises a needle.

19. Catheter of claim 17 further comprising a stiffening mandrel extending through said tube.

20. Catheter of claim 17 wherein a stiffening mandrel extends along an exterior of said tube.

21. A catheter for delivering a drug to a location within a patient, comprising:
   a guide wire lumen;
   a tube extending from a proximal end to a distal end along an axis of said guide wire lumen and having a first lumen for receiving said drug, said first lumen extending from the proximal end of said tube to an injection port;
   a preferential bending point on said tube; and
   an inflatable balloon for rotating said injection port away from the axis of the guide wire lumen by bending said tube at said preferential bending point;
   said injection port being coupled to said tube at said preferential bending point.

22. Catheter of claim 21 wherein said injection port comprises a needle.

23. Catheter of claim 21 further comprising a stiffening mandrel extending through said tube.

24. Catheter of claim 21 wherein a stiffening mandrel extends along an exterior of said tube.

25. Method for delivering medication to a patient comprising the steps of:

inserting a catheter into a patient, said catheter comprising a catheter body, a guide wire lumen having an axis, a tube, a drug delivery lumen within the tube, and an injection port in communication with said drug delivery lumen;

angularly extending the injection port away from the axis of the guide wire lumen toward or into the patient's artery wall by inflating a balloon to bend said tube at a preferential bending point, said injection port being attached to said tube at said preferential bending point, to change an angle formed between said injection port and said axis of the guide wire lumen; and injecting medication into the patient through the drug delivery lumen and said injection port.

26. Method of claim 25 wherein said injection port comprises a needle.

27. Method of claim 25, further comprising the steps of:

moving said injection port toward an angle parallel with said axis of the guide wire lumen after said step of injecting; and retracting said catheter.

* * * * *